United States Patent [19]

Badorc et al.

[11] Patent Number: 5,190,938

[45] Date of Patent: Mar. 2, 1993

[54] DERIVATIVES OF 2-HYDROXYTHIOPHENE AND -FURAN FUSED WITH A NITROGEN-CONTAINING RING AND THEIR APPLICATION IN THERAPY

[75] Inventors: Alain Badorc, Roquettes; Marie-Françoise Bordes, Labarthe sur Seze; Daniel Frehel, Toulouse; Jean-Marc Herbert, Plaisance du Touch, all of France

[73] Assignee: Sanofi, Paris, France

[21] Appl. No.: 591,828

[22] Filed: Oct. 2, 1990

[30] Foreign Application Priority Data

Oct. 2, 1989 [FR] France ............................ 89 12854

[51] Int. Cl.$^5$ ............... A61K 31/435; C07D 495/04
[52] U.S. Cl. ........................ 514/215; 514/301; 514/302; 514/412; 540/593; 546/114; 546/116; 548/453; 544/127; 544/362
[58] Field of Search ............... 546/114, 116; 540/593; 548/453; 514/215, 301, 302, 412; 544/127, 362

[56] References Cited

U.S. PATENT DOCUMENTS

| | | | |
|---|---|---|---|
| 4,414,225 | 11/1983 | Sauter et al. | 540/593 |
| 4,424,356 | 1/1984 | Maffrand et al. | 546/114 |
| 4,740,510 | 4/1988 | Badorc et al. | 546/114 |

FOREIGN PATENT DOCUMENTS 0058341 2/1981 European Pat. Off.
0054442 10/1981 European Pat. Off.
0192535 1/1986 European Pat. Off.

OTHER PUBLICATIONS

Low et al., Burger's Medicinal Chem. 4th Ed., Part I—The Basis of Medicinal Chem., John-Wiley, pp. 107 & 177-182 (1980).

*Primary Examiner*—Bernard Dentz
*Attorney, Agent, or Firm*—Wegner, Cantor, Mueller & Player

[57] ABSTRACT

The invention relates to compounds of formula

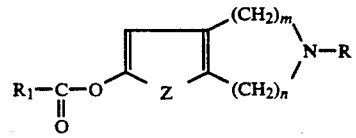

in which $R_1$ is selected from the groups $R_3$ and $OR_3$, R is selected from H and a group $CHR_2R'$, in which $R_2$ is selected from H, alkyl, carboxy and carboxamido and R', is H, alkyl or phenyl, Z represents S or O; and m and n, which may be identical or different, equal 1 or 2, and their N-oxides, salts and quaternary ammonium derivatives.

The invention also relates to the process for preparing these compounds, as well as to pharmaceutical compositions containing them.

10 Claims, No Drawings

DERIVATIVES OF 2-HYDROXYTHIOPHENE AND -FURAN FUSED WITH A NITROGEN-CONTAINING RING AND THEIR APPLICATION IN THERAPY

The present invention relates to derivatives of 2-hydroxythiophene and -furan fused with a heterocyclic amine, of formula
in which $R_1$ is selected from the groups $R_3$ and $OR_3$, in which $R_3$ is selected from $C_1$ to $C_6$ alkyl, phenyl and benzyl;

R is selected from H and a group $CHR_2R'$, in which $R_2$ is H, $C_1$ to $C_4$ alkyl, $-COOR_4$, $R_4$ being selected from H, $C_1$ to $C_4$ alkyl and benzyl, and $-CONR_5R_6$, $R_5$ and $R_6$, independently of one another, being selected from H, $C_1$ to $C_4$ alkyl and benzyl, or $R_5$ and $R_6$, with the nitrogen to which they are attached, forming a saturated $C_4$-$C_8$ heterocycle, in particular piperidino, 1-pyrrolidinyl, morpholino and 1-piperazinyl; R' is H, $C_1$ to $C_4$ alkyl or substituted or unsubstituted phenyl;

Z represents S or O; and m and n, which are the same or different, are 1 or 2, as well as the N-oxides of these compounds, the salts of the amino groups and of their oxides with pharmaceutically acceptable acids, and the quaternary ammonium derivatives formed with $C_1$ to $C_4$ alkyl halides and sulphates and the amino groups.

The phenyl groups may be substituted with halogen atoms, $C_1$ to $C_4$ alkyl or alkoxy, trifluoromethyl group or nitro.

The invention also relates to the processes for producing these compounds and to pharmaceutical compositions comprising these compounds.

The compounds of formula I in which $R_1$ is $C_2$ to $C_4$ alkyl are preferred, and more particularly, when Z is S, $R_2$ is H and R' a phenyl group, substituted or not.

The compounds of formula I according to the invention may be prepared by O-acylation of the compounds of formula II

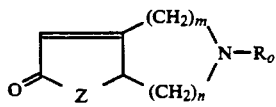

in which Z, m and n have the same meaning as in the formula I and $R_o$ represents a group protecting the amino function such that the N—$R_o$ bond is stable in the presence of a strong base and $R_o$ is removable in an acid medium, such as, for example, the trityl or tert-butyloxycarbonyl groups, the acylation being followed by removal of the group $R_o$ by reaction with an anhydrous acid so as to obtain a compound of formula III

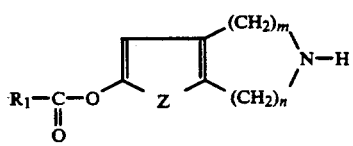

and, when R is other than H, this compound being reacted with a compound of formula

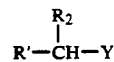

in which Y is halo or $R_7SO_3$, $R_7$ being selected from $C_1$ to $C_4$ alkyl and phenyl groups.

The acylation can be performed, in particular, by reaction of a suitable acid halide, acid anhydride, chloroformate or carbonate with enolate of formula IV

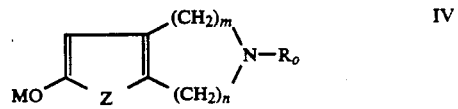

in which M represents an alkali metal cation, which is obtained by reaction of a strong base, such as butyllithium, an alkali metal tert-butylate or an alkali metal hydride, with the compound of formula II; the reaction is performed in an inert solvent such as an ether, for example tetrahydrofuran, an aliphatic hydrocarbon, for example hexane or pentane, or mixtures thereof, at a temperature from about $-5°$ C. to about 30° C. and preferably in an inert atmosphere.

In the case where the group $R_o$ is a protective group, its removal is performed by reaction with trifluoroacetic acid, pure or in a solvent such as dichloromethane, at room temperature, or by reaction with hot acetic acid or alternatively by the action with a halohydric acid in an organic solvent, such as 3N HCl in $CH_3COOC_2H_5$.

The alkylation of the nitrogen of the compound of formula III is performed under the usual conditions with the appropriate halide or sulfonate Y—$CHR_2R'$ in the presence of a base such as $NaHCO_3$ or $KHCO_3$, in a polar aprotic solvent such as tetrahydrofuran or dimethylformamide, preferably in an inert atmosphere and at a temperature from about 20° C. to about 90° C.

In cases where $R_2$ is H or $C_1$ to $C_4$ alkyl, it is also possible to perform the acylation of a compound of formula II in which $R_o$ is —$CHR_2R'$, R' being as defined above, to obtain a compound of formula I directly.

When $R_1$ is $CH_3$, the acylation of the compound of formula II may also be performed by reaction of an excess of isopropenyl acetate

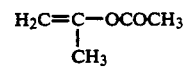

with the compound of formula II in the presence of an acid catalyst, optionally in a solvent such as an ether, for example tetrahydrofuran, or a hydrocarbon such as benzene or petroleum ether; the acid catalysts are, in particular, benzenesulphonic or para-toluenesulphonic acids; the reaction is preferably performed at the refluxing temperature of the solvent.

The N-oxides (amine-oxides) of the compounds of formula I are prepared by reaction of an organic peracid with the amine of formula I under usual conditions. The oxidation can, in particular, be performed by reaction of at least one molar equivalent of the commercial peracids: peracetic acid, perbenzoic acid or 3-chloroperbenzoic acid, with the amine of formula I in an inert solvent such as dichloromethane or chloroform, at a temperature from $-5°$ C. to 30° C.; peracids prepared immediately before use by known methods may also be employed.

The N-oxides are not very stable, and they are preferably isolated in the form of one of their addition salts with an acid, in particular a hydrohalic acid, HCl or HBr; to this end, an acid is introduced into the oxidation medium at the end of the reaction, and then the formed salt is precipitated by adding a solvent in which it is insoluble, such as ethyl ether.

The quaternary ammonium salts are prepared by conventional means by reaction of an alkyl halide or sulphate with the amine of formula I, in a solvent.

Finally, the amine salts of the compounds of formula I are obtained by reacting at least one equivalent of the pharmaceutically acceptable acid with the amine of formula I in a solvent, and are recovered in a conventional manner by precipitation or removal of the solvents.

Some of the compounds of formula II are known; the others may be prepared by applying methods already described for similar compounds.

Thus, the compound of formula II in which $Z=S$, $m=1$, $n=2$ and $R_o=C(C_6H_5)_3$ is described in Patent FR-A-2,576,901; compounds for which $Z=S$, $m=1$, $n=2$ and $R_o=CH_2R'$ are described in FR-A-2,508,459, while compounds in which $Z=S$, $m=1$, $n=2$ and $R_o=R'—CH—COOR$ are described in FR-A-2,576,901.

The compounds for which $Z=S$, $m=2$ and $n=1$ are prepared by applying the same methods.

Compound of formula II wherein $Z=O$, $m=2$, $n=1$ and $R_o=COOCH_2C_6H_5$ is described in Chem. Pharm. Bull. 30(3) p. 1084–87 (1982), and the general principle of its method of preparation may be applied for preparing, for example, the compounds in which $R_o=C(C_6H_5)_3$, $COO(t-C_4H_9)$ or $CH_2R'$.

The compounds of formula II in which $Z=O$, $m=1$, $n=2$ and $R_o$ is $CH_2R'$ or a protective group may be prepared by the aminoalkylation of glyoxylic acid, applying a method described by J. Schreiber et al in Bull. Soc. Chim. France (1963) p. 625–629, according to the following reaction scheme:

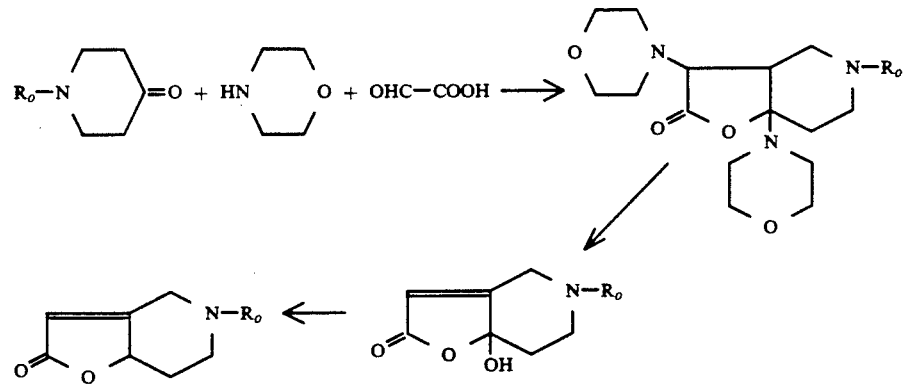

The compounds of formula II in which $Z=S$, $m=1$, $n=1$ and $R_o$ is $CH_2R'$ or a protective group may be prepared from thiophenealdehyde applying the following reaction scheme:

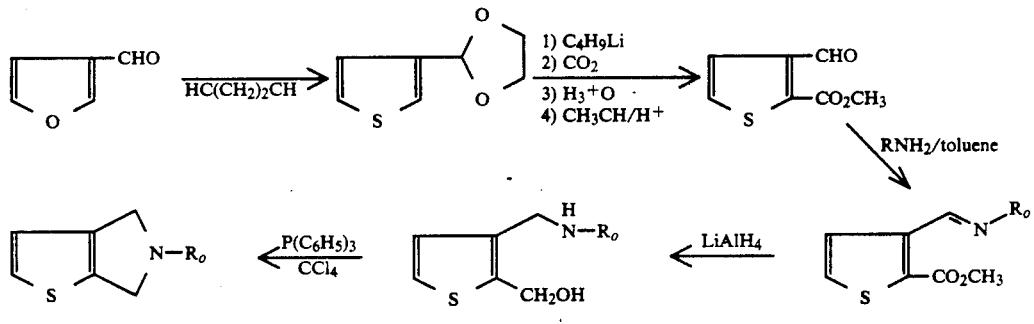

Compounds of formula II in which $R_o$ represents $R'—CH—R_2$, $Z=S$, $m=1$, $n=2$ and $R'$ is a phenyl group are known, and are blood platelet aggregation inhibitors and antithrombotic agents: the compounds in which $R_2$ represents $COOR_4$ or $—CONR_5R_6$ are claimed in Patent FR-A-2,576,901, while the compounds in which $R_2$ represents H are claimed in Patent FR-A-2,495,156.

The compounds of the invention, for their part, are inhibitors of pancreatic and leucocyte elastases, proteolytic enzymes capable of hydrolyzing most components of connective tissues, and most especially elastin.

The involvement of leucocyte elastase in the pathogenesis of certain diseases and accordingly the usefulness of its inhibitors have been stressed; reference may be made, in particular, to the short review published in Annual Reports in Medicinal Chemistry vol. 20, p. 237 to 246 (1985).

Thus, the administration of elastase inhibitors is known to decrease the destruction of pulmonary tissue in pulmonary emphysema as well as in cystic fibrosis.

It has also been shown that the changes in the blood vessels with ageing were linked in part to an increase in the synthesis of an elastase in their wall, bringing about degradation of the connective tissue of the vascular wall promoting the formation of atheroma plaques. The administration of an elastase inhibitor will hence be useful in the prevention and treatment of atherosclerosis.

Finally, an imbalance has recently been demonstrated between proteases having an elastolytic activity and their natural inhibitors in degenerative rheumatic disorders and some inflammatory conditions. Thus, by reestablishing the biological balance of these enzymes, the administration of an elastase inhibitor will be useful in the treatment of these diseases.

Furthermore, the administration of an inhibitor of pancreatic elastase is known to be useful in the treatment of acute pancreatitis.

Moreover, some of the compounds of the invention, and in particular the compounds of formula I in which $Z=S$, $m=1$, $n=2$ and $R_2=H$ or COOR, with $R_4=C_1-C_4$-alkyl and $R'=$aryl, have, in addition, an antithrombotic activity, sometimes combined with a platelet aggregation-inhibitory activity.

In view of the pharmacological activities of the compounds according to the invention, the pharmaceutical compositions comprising them will be useful, in particular, in the treatment of pulmonary emphysema, cystic fibrosis atherosclerosis and inflammatory joint conditions, and in all conditions where there is a pathological imbalance between elastases and their natural inhibitors.

Pharmaceutical compositions comprising at least one compound of formula I, its N-oxide, their salts with a pharmaceutically acceptable inorganic or organic acid or its quaternary ammonium derivatives, combined with the usual excipients or vehicles, are accordingly another subject-matter of the invention. These compositions may be administered by the usual routes, in particular orally, for example in the form of tablets, hard gelatin capsules, granules or solutions, or by injection; the pharmaceutical dosage forms will be prepared by methods well known to the person skilled in the art, with compatible conventional excipients The daily dosage may be namely between 10 and 250 mg of active ingredient by the oral route.

In the following, illustrative examples of compounds of the invention and of processes for preparing these are provided, together with the results of a pharmacological evaluation.

The elemental analyses and the infrared and NMR (internal reference tetramethylsilane) spectra are consistent with the structure of the products isolated.

EXAMPLE 1

Compound of formula I in which $Z=S$; $m=1$; $n=2$; $R_2=H$; $R'=2\text{-ClC}_6H_4$; $R_1=CH_3$ (reference: PCR 3927).

a) 5-(2-chlorobenzyl)-5,6,7,7a-tetrahydro-4H-thieno[3,2-c]pyridine-2-one formula II: $Z=S$; $m=1$; $n=2$; $R=CH_2(2\text{-ClC}_6H_4)$).

79 cm$^3$ of a 12% solution of butyllithium in hexane (0.147 mole) are introduced dropwise into a solution, cooled to $-20°$ C., of 32.6 g (0.123 mole) of 5-(2-chlorobenzyl)-4,5,6,7-tetrahydrothieno[3,2-c]pyridine in 320 cm$^3$ of tetrahydrofuran. When the addition is complete, the lithium derivative precipitates and the temperature is allowed to return to 0° C. 15 cm$^3$ of hexamethylphosphoric triamide (HMPT) are then added: the precipitate becomes deep red.

The temperature is lowered to $-40°$ C. and a solution of tributyl borate (39.8 cm$^3$=0.147 mole) in 40 cm$^3$ of anhydrous tetrahydrofuran is added dropwise in the course of half an hour. The precipitate disappears and the reaction medium becomes light yellow. The temperature is maintained at $-40°$ C. for half an hour then brought to 10° C. and maintained for 2 hours at this temperature. 33 cm$^3$ (0.291 mole) of 30% hydrogen peroxide are added dropwise while the temperature of the medium is maintained below 30° C. A copious precipitate is formed during the addition. Stirring is maintained for 1 hour at room temperature. The reaction medium is poured into water, the product is extracted with 3×200 cm$^3$ of ethyl ether and the organic phases are dried over sodium sulphate and concentrated under vacuum at a temperature below 40° C. The residual liquid is chromatographed on a silica column (eluent: cyclohexane/ethyl acetate, 6:4) to remove the remaining HMPT.

After evaporation to dryness, the residue is treated with one molar equivalent of oxalic acid in acetone, and the light yellow crystals formed are filtered off.

On recrystallization in ethanol, beige-coloured crystals of oxalate are obtained.

yield: 52%, m.p. 170° C.

Base: m.p. 73°-74.5° C. (ethanol)

NMR (CDCl$_3$) 7.1–7.6(m,4H); 6.2(s,1H); 4.2–4.7(m,1H); 3.9(s,2H); 1.5–4.2(m,6H).

b) 5-(2-chlorobenzyl)-5,6,7,7a-tetrahydro-4H-thieno[3,2-c]pyrid-2-yl acetate.

8.85 g (0.0316 mole) of 5-(2-chlorobenzyl)-5,6,7,7a-tetrahydro-4H-thieno[3,2-c]pyridine-2-one are dissolved in 120 ml of isopropenyl acetate with 7.8 g (0.0411 mole) of p-toluenesulphonic acid; the medium is stirred at 90° C. for 6 hours. After cooling to about 20° C., 2 volumes of water are introduced into the medium, the pH is made basic by adding saturated aqueous NaHCO$_3$ solution and the desired product is extracted with ethyl acetate.

After removal of the solvent, the oil, dissolved in CH$_2$Cl$_2$, is filtered on silica to give a 68% yield of the ester, which melts at 68° C.

$^1$HNMR : (60MHz, CDCl$_3$) 2.20(s,3H); 2.63–2.95(m,4H); 3.51(s,2H); 3.80(s,2H); 6.27(s,1H); 7.07–7.67(m,1H).

EXAMPLE 2

Compound of formula I in which $Z=S$; $m=1$; $n=2$; $R_2=H$; $R'=2\text{-ClC}_6H_4$; $R_1=(CH_3)_3C$ (reference: SR 26766).

10.7 ml (0.017 mole) of a 1.6M solution of butyllithium in hexane are added dropwise at 0° C. to a solution of 4.55 g (0.0162 mole) of 5-(2-chlorobenzyl)5,6,7,7a-tetrahydro-4H-thieno[3,2-c] pyridine-2-one in 45 ml of tetrahydrofuran.

After 15 minutes, stirring, still at 0° C., 2.04 ml (0.0166 mole) of pivaloyl chloride are introduced dropwise and the medium is then stirred for 1 hour 30 minutes at room temperature, i.e. about 20° C. 2 volumes of water are then introduced and the final product is extracted in ethyl acetate; the oil, isolated after washing the organic phase with water and evaporating off the solvent, is chromatographed on a silica column, eluting with a toluene/ethyl acetate mixture (9:1 v/v). The hydrochloride of the final product, isolated in a 57% yield, melts at 214° C.

It is also possible to prepare the thienopyridone enolate as follows: 5 g (0.0179 mole) of thienopyridine-one, in solution in 50 ml of tetrahydrofuran, are introduced slowly at 5° C. into 20 ml of this same solvent containing 2.11 g (0.0188 mole) of potassium tert-butylate. After stirring for a few minutes, 2.3 ml (0.0188 mole) of pivaloyl chloride are added. After 2 hours' stirring at room temperature, 2 volumes of water and then 2 volumes of ethyl acetate are added to the medium. After stirring, the organic phase is separated after settling has taken place, washed with water and dried, the solvent is removed and the pure final product is isolated as above.

EXAMPLES 3 to 12

The compounds of formula I wherein $Z=S$, $m=1$, $n=2$ whose characteristics are as follows are prepared by one of the methods described in Example 2, employing the acid chloride $R_1COCl$, $R_1$ being as defined above:

| Ex. | SR or PCR | $R_1$ | $R_2$ | R' | M.p. (hydrochloride) | Yield of salt |
|-----|-----------|-------|-------|-----|----------------------|---------------|
| 3 | PCR4094 | $CH_3(CH_2)_2$ | H | 2-$ClC_6H_4$ | 181° C. | 65% |
| 4 | SR26772 | $(CH_3)_2CH$ | H | 2-$ClC_6H_4$ | 189° C. | 60% |
| 5 | 26851 | $(CH_3)_2CHCH_2$ | H | 2-$ClC_6H_4$ | 190° C. | 45% |
| 6 | 26769 | $(CH_3)_2CH$ | H | 4-$ClC_6H_4$ | 220° C. | 48% |
| 7 | 26768 | $(CH_3)_3C$ | H | 4-$ClC_6H_4$ | 248° C. | 61% |
| 8 | 26767 | $CH_3(CH_2)_2$ | H | 4-$ClC_6H_4$ | 225° C. | 65% |
| 9 | 26829 | $(CH_3)_2CH$ | H | $C_6H_5$ | 220° C. | 30% |
| 10 | 26827 | $(CH_3)_3C$ | H | $C_6H_5$ | 234° C. | 40% |
| 11 | 27261 | $(CH_3)_3C$ | H | 4-$OCH_3C_6H_4$ | 255° C. | 85% |
| 12 | 26915 | $C_6H_5$ | H | 2-$ClC_6H_4$ | 202° C. (oxal.) | 49% |

The NMR chemical shifts of the compounds of examples 3 to 12 are described in the following:

| Ex. (salt) | $^1$H NMR - δ (ppm): |
|-----------|----------------------|
| 3 (HCl) | (80 MHz, DMSO-$d_6$: 1.05(t, 3H); 1.44–2.01(m, 2H); 3.04–3.95(m, 4H); 4.30(s, 2H); 4.70(s, 2H); 6.73(s, 1H); 7.43–7.84(m, 3H); 8.06–8.34(m, 1H) |
| 4 (HCl) | (80 MHz, DMSO-$d_6$; 1.29(d, 6H); 3.04(h, 1H); 3.15–3.68(m, 4H); 4.28(s, 2H); 4.69(s, 2H); 6.72(s, 1H); 7.51–7.65(m, 3H); 8.14–8.24(m, 1H) |
| 5 (HCl) | (250 MHz, DMSO-$d_6$): 0.94(d, 6H); 2.07(m, 1H); 2.49(d, 2H); 3.03–3.66(m, 4H); 4.18(s, 2H); 4.59(s, 2H); 6.61(s, 1H); 7.46–7.60(m, 3H); 8.06–8.34(m, 1H) |
| 6 (HCl) | (80 MHz, DMSO-$d_6$: 1.31(d, 6H); 2.97(h, 1H); 3.16–3.82(m, 4H); 4.19(s, 2H); 4.57(s, 2H); 7.64(d, 2H); 7.82(d, 2H) |
| 7 (HCl) | (80 MHz, DMSO-$d_6$): 1.36(s, 9H); 2.97–3.67(m, 4H); 4.17(s, 2H); 4.57(s, 2H); 6.69(s, 1H); 7.73(d, 2H); 7.84(d, 2H) |
| 8 (HCl) | (80 MHz, DMSO-$d_6$): 1.03(t, 3H); 1.72(m, 2H); 2.66(t, 2H); 4.13(s, 2H); 4.54(s, 2H); 6.68(s, 1H); 7.64(d, 2H); 7.84(d, 2H) |
| 9 (HCl) | (250 MHz, DMSO-$d_6$): 1.19(d, 6H); 2.85(h, 1H); 3.04–3.12(m, 2H); 3.51–3.66(m, 2H); 4.07(s, 2H); 4.41–4.47(m, 2H); 6.60(s, 1H); 7.46–7.48(m, 3H); 7.64–7.66(m, 2H) |
| 10 (HCl) | (250 MHz, DMSO-$d_6$): 1.26(s, 9H); 3.03–3.66(m, 4H); 4.09(s, 2H); 4.45(s, 2H); 6.61(s, 1H); 7.47–7.49(m, 3H); 7.62–7.64(m, 2H) |
| 11 (HCl) | (250 MHz, DMSO-$d_6$): 1.27(s, 9H); 2.96–3.19(m, 2H); 3.52–3.74(m, 2H); 3.81(s, 3H); 4.03(s, 2H); 4.38(s, 2H); 6.61(s, 1H); 7.06(d, 2H); 7.58(d, 2H) |
| 12 (amine) | (80 MHz, DMSO-$d_6$) 2.74–3.21(m, 4H); 3.75(s, 2H); 4.05(s, 2H); 6.77(s, 1H); 7.33–7.93(m, 7H); 8.06–8.34(m, 2H) |

The intermediate thienopyridines-one were prepared by the method described in Example 1a) and isolated in their salt form:
5-(4-chlorobenzyl)-5,6,7,7a-tetrahydro-4H-thieno[3,2-c]pyridine-2-one, maleate melts at 158° C.,
5-benzyl-5,6,7,7a-tetrahydro-4H-thieno[3,2-c]pyridine-2-one, maleate melts at 132° C.,
5-(4-methoxybenzyl)-5,6,7,7a-tetrahydro-4H-thieno-[3,2-c]pyridine-2-one, oxalate melts at 125° C.

EXAMPLE 13

Compound of formula I in which $Z=S$; $m=1$; $n=2$; $R_2=CH_3$; $R'=C_6H_5$; $R_1=C(CH_3)_3$ (reference : SR 27319).

a) 5-(1-phenylethyl)-5,6,7,7a-tetrahydro-4H-thieno[3,2-c]pyridine-2-one (compound of formula II in which $Z=S$; $m=1$; $n=2$; $R_o = CH(CH_3)C_6H_5$).

10.43 g (0.104 mole) of potassium hydrogenocarbonate and 7.82 g (0.052 mole) of sodium iodide followed by 9.8 g (0.053 mole) of (1-bromoethyl)benzene are added to a solution of 10 g (0.052 mole) of 5,6,7,7a-tetrahydro-4H-thieno[3,2-c]pyridine-2-one, hydrochloride in 100 ml of dimethylformamide. The medium is maintained at 60° C. for 90 minutes and then poured into 600 ml of water. The final product is extracted in ethyl acetate. Yield 66%.

b) The ester of formula I is prepared via the lithium derivative of the thienopyridine-one, by the method described in Example 2. The hydrochloride, a mixture of stereoisomers, melts at 133° C.

$^1$H NMR (250 MHz, DMSO-$d_6$) : 1.25(d,9H); 1.74–1.80(m,3H); 2.82–2.95(m,1H); 2.95–3.10(m,1H); 3.25–3.45(m,2H); 3.90–4.05(m,1H); 4.05–4.20(m,1H); 4.40–4.55(m,1H); 4.57–4.70 (m,1H); 6.55(d,1H); 7.45(s,3H); 7.66–7.75(m,2H); 11.80–12.00(d,1H).

EXAMPLES 14 and 15

The compounds of formula I in which $Z=S$; $m=1$; $n=2$; $R'=H$; $R_1=-C(CH_3)_3$ and $R_2=H$ or $R_2=CH_2CH_3$, the characteristics of which are as follows, are prepared by the method described in Example 13:

a) Ex. 14 (SR 26984):
5-methyl-4,5,6,7-tetrahydrothieno[3,2-c]pyrid-2-yl t-butyrate: the oxalic acid salt of this compound obtained by reaction of 1 molecule of oxalic acid per molecule of the amine of formula I melts at 170° C.

$^1$H NMR (250 MHz,DMSO-$d_6$) : 1.27(S,9H); 4.80(s,3H); 2.97 (t,2H); 3.36(t,2H); 4.05(s,2H); 6.60(s,1H).

The oxalate of the starting thienopyridine-2-one melted at 145° C.

b) Ex. 15 (SR 27318) :
5-propyl-4,5,6,7-tetrahyirothieno[3,2-c]pyrid-2-yl t-butyrate: the hydrochloride of this compound melts at 190° C.

$^1$H NMR (250 MHz, DMSO-$d_6$) : 0.95(t,3H); 1.30(s,9H); 1.72–1.87(m,2H); 3.05–3.17(m,5H); 3.60–3.70 (m, 1H); 4.00–4.05 (m,1H); 4.30(d,1H); 6.58(s,1H); 11.35(s,1H).

EXAMPLE 16

Compound of formula I in which Z=S; m=1; n=2; R=H; R$_1$=—C(CH$_3$)$_3$ (reference SR 26842).

a) 5-trityl-4,5,6,7-tetrahydrothieno[3,2-c]pyrid-2-yl t-butyrate:

Prepared by the method described in Example 2, starting with 5-trityl-5,6,7,7a-tetrahydro-4H-thieno[3,2-c]pyridine-2-one (m.p. 210° C., prepared as in FR-A-2,576,901), butyllithium and pivaloyl chloride.

b) 4,5,6,7,-tetrahydrothieno[3,2-c]pyrid-2-yl t-butyrate:

1.3 g of derivative obtained according to a) are dissolved in 10 ml of methylene chloride, and 1 ml of trifluoroacetic acid is added dropwise; after 30 minutes, stirring, the mixture is poured into at least 3 equivalents of a 5.8N solution of HCl in ethyl ether; the precipitate formed is isolated.

The hydrochloride of this compound, which melts at 211° C., is thereby obtained in a 74% yield. $^1$H NMR (250 MHz, DMSO-d$_6$): 1.27(s,9H); 2.92-2.96(m,2H); 3.33-3.39(m,2H); 4.05(s,2H); 6.61(s,1H).

EXAMPLE 17

Compound of formula I in which Z=S; m=1; n=2 R=H, R$_1$=(CH$_3$)$_2$CH (reference SR 26861).

4,5,6,7-Tetrahydrothieno[3,2-c]pyrid-2-yl isobutyrate, hydrochloride obtained by the method described in Example 16, replacing pivaloyl chloride by isobutyryl chloride, melts at 181° C.

EXAMPLE 18

Compound of formula I in which Z=O; m=1; n=2; R$_2$=H; R'=2-ClC$_6$H$_4$; R$_1$=—C(CH$_3$)$_3$ (reference SR 26938).

a) 5-(2-chlorobenzyl)-3,7a-dimorpholino-3a,4,5,6,7,7a-hexahydro-3H-furo[3,2-c]pyridine-2-one:

31.16 g (0.358 mole) of morpholine are added dropwise to a solution, cooled to 0° C., of 16.46 g (0.179 mole) of glyoxylic acid, monohydrate in 40 cm$^3$ of 95% ethanol. The mixture is allowed to return to room temperature and 40 g (0.179 mole) of N-(2-chlorobenzyl)-4-piperidine-one are rapidly added portionwise. A partial dissolution is observed and then a precipitate is formed in the reaction medium.

The mixture is stirred for 3 hours at room temperature and 100 ml of water are added; the precipitate formed is filtered off and washed with water and then with isopropanol.

After drying, 31.8 g of white powder, m.p. 173° C., are collected (yield: 41%).

b) 5-(2-chlorobenzyl)-7a-hydroxy-5,6,7,7a-tetrahydro-4H-furo[3,2-c]pyridine-2-one, hydrochloride:

50 cm$^3$ of aqueous solution of 3N Hcl are added to a solution of 21 g (0.048 mole) of product obtained in the preceding step, and the mixture is maintained at its refluxing temperature for one hour; a precipitate appears in the medium. The latter is cooled to room temperature and the precipitate is isolated; it is then washed with cold water and thereafter with ethanol and dried; 12 g of white powder, which melt with decomposition at about 220°-230° C., is recovered (yield: 78%).

c) 5-(2-chlorobenzyl)-5,6,7,7a-tetrahydro-4H-furo[3,2-c]pyridine-2-one:

0.6 g (0.0158 mole) of sodium borohydride is added portionwise to 10 g (0.0316 mole) of 5-(2-chlorobenzyl)-7a-hydroxy-5,6,7,7a-tetrahydro-4H-furo[3,2-c]pyridine-2-one, hydrochloride in 350 cm$^3$ of 0.1N aqueous sodium hydroxide; the medium is stirred at room temperature for 3 hours. 100 cm$^3$ of 12N hydrochloric acid are then added. After one hour at room temperature, the pH of the medium is brought to approximately 8 by adding sodium hydrogenocarbonate in powder form; the final product is then extracted with ethyl ether; the organic phase is washed with water, then dried over sodium sulphate and evaporated to dryness.

A colourless resin is recovered, which is solidified in isopropyl ether.

7.5 g of white powder, m.p. 74° C., are recovered (yield: 90%).

d) 5-(2-chlorobenzyl)-4,5,6,7-tetrahydrofuro-[3,2-c]pyrid-2yl t-butyrate is prepared from the product obtained in the preceding step, by the method of Example 2 with potassium tert-butylate and pivaloyl chloride. The hydrochloride melts at 160° C.

$^1$H NMR (80 MHz, DMSO-d$_6$): 1.35(s,9H); 3.00-3.20(m,2H); 3.55-3.90(m,2H); 4.10(s,1H); 4.70(s,1H); 6.05(s,1H); 7.50-7.80(m,3H); 8.10-8.30(m,1H).

EXAMPLE 19

Compound of formula I in which Z=S; m=1, n=2; R$_2$=COOCH$_3$; R'=2-ClC$_6$H$_4$; R$_1$=CH$_3$ (reference SR 26571).

This compound is obtained in a 98% yield by the action of isopropenyl acetate on methyl α{2-oxo-2,4,5,6,7,7a-hexahydrothieno[3,2-c]pyrid-5-yl}-(2 -chlorophenyl) acetate, applying the method described in Example 1.

Amine: $^1$H NMR (250 MHz, CDCl$_3$): 2.23(s,3H); 2.73-2.77 (m,2H); 2.85-2.89(m,2H); 3.51(d,1H); 3.64(d,3H); 3.69 (s,1H); 4.89(s,1H); 5.27(s,1H); 7.22-7.41(m,3H); 7.64-7.68(m,1H).

The hydrochloride melts at 96° C.

The starting material is prepared in a 58% yield by the method described in Example 13a), reacting 11.65 g of methyl α-chloro-(2-chlorophenyl)acetate instead of (1-bromoethyl)benzene; its hydrochloride melts at 130° C.

EXAMPLE 20

Compound of formula I in which Z=S; m=1; n=2; R$_2$=COOCH$_3$; R'=2-ClC$_6$H$_4$; R$_1$=C(CH$_3$)$_3$ (reference SR 26859):

1.3 g (0.0047 mole) of 4,5,6,7-tetrahydrothieno-[3,2-c]pyrid-2-yl t-butyrate hydrochloride, obtained in Example 16, are dissolved in 30 ml of dimethylformamide with 0.94 g (0.0094 mole) of KHCO$_3$ and 1.24 g (0.047 mole) of methyl 2-bromo-(2-chlorophenyl)acetate. The medium is kept stirring at 60° C. for 2 hours and then poured into a mixture of 2 volumes of water and 2 volumes of ethyl acetate; the organic phase is separated after settling has taken place. The oil remaining after removal of the solvent is chromatographed on a silica column, eluting with a toluene/ethyl acetate mixture (9:1). The hydrochloride of the final product, isolated in a 66% yield, melts at 103° C.

$^1$H NMR (250 MHz, DMSO-ds): 1.39(s,9H); 3.05(m,2H); 3.43 (m,2H); 3.84(s,3H); 4.12(s,2H); 5.54(s,1H); 6.66(s,1H); 7.71-7.75(m,3H); 7.93-7.95(m,1H).

EXAMPLE 21

Compound of formula I in which Z=S; m=1; n=2; R$_2$=COOCH$_3$; R'=2-ClC$_6$H$_4$; R$_1$=CH(CH$_3$)$_2$ (reference SR 26886).

Prepared in an 80% yield by the action of isobutyryl chloride on the compound (SR 26861), by the method described in Example 20. The hydrochloride of this compound melts at 111° C.

$^1$H NMR (250 MHz, DMSO-d$_6$): 1.77(d,6H); 2.83(h,1H); 2.99 (m,2H); 3.42(m,2H); 3.72(s,3H); 4.11(s,2H); 5.58(s,1H); 6.56(s,1H); 7.48–7.65(m,3H); 7.90–7.94(m,1H).

EXAMPLE 22

Compound of formula I in which Z=S; m=1, n=2;

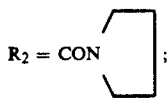

R'=2-ClC$_6$H$_4$; R$_1$=CH$_3$ (reference SR 26913).

This compound is prepared in a 43% yield by reacting, according to the method described in Example 1, isopropenyl acetate with N-{α-(2-oxo-2,4,5,6,7,7a-hexahydrothieno[3,2-c]pyrid-5-yl)-(2-chlorophenyl)acetyl}pyrrolidine, obtained by applying the method described in Example 11 of Patent FR-A-2,576,901.

The hydrochloride, prepared in ethyl ether, melts at 135° C.

$^1$H NMR (80 MHz, DMSO-ds): 1.72–2.14(m,4H); 2.45(s,3H); 2.71–4.74(m,10H); 5.96(s,1H); 6.77(s,1H); 7.41–8.17 (m,4H).

EXAMPLE 23

Compound of formula I in which Z=S; m=2; n=1; R$_2$=H; R'=2-ClC$_6$H$_4$; R$_1$=CH(CH$_3$)$_2$ (reference SR 26862).

a) 6-(2-chlorobenzyl)-5,6,7,7a-tetrahydro-4H-thieno[2,3-c]pyridine-2-one:

210.4 cm$^3$ (0.337 mole) of a 1.6M solution of butyllithium in hexane are added dropwise to a solution, cooled to 0° C., of 74 g (0.280 mole) of 6-(2-chlorobenzyl)-4,5,6,7-tetrahydrothieno[2, 3-c]pyridine, prepared as in J. Heterocyclic Chem., 13, 1347 (1976), in 740 cm$^3$ of tetrahydrofuran. When the addition is complete, the mixture is allowed to return to room temperature and is stirred for 15 minutes. The reaction medium is then cooled to −20° C. and 90.8 cm$^3$ (0.337 mole) of tributyl borate in 100 cm$^3$ of tetrahydrofuran are added dropwise. When the introduction is complete, the mixture is stirred for 1 hour at 10° C. The temperature is then lowered to −40° C. and 79 cm$^3$ (0.700 mole) of 30% hydrogen peroxide are added dropwise. An intense precipitate forms during the addition. The reaction medium is allowed to return to room temperature; after stirring overnight, the mixture has become homogeneous. 2 volumes of water are then introduced and the final product is extracted in dichloromethane. The organic phase is washed with water and dried. Evaporation of the solvent leads to a residue, which is purified by filtration on a silica bed (elution with dichloromethane). The hydrochloride of the final product melts at 110° C. (yield: 93%). $^1$H NMR (80 MHz, DMSO-d$_6$): 2.93–4.28(m,6H); 4.56(s,2H); 5.07–5.33(m,1H); 6.47(s,1H); 7.44–7.66(m,3H); 7.96–8.18 (m,1H).

b) 12.7 ml (0.020 mole) of a 1.6M solution of butyllithium in hexane are added dropwise at 0° C. to a solution of 5.15 g (0.019 mole) of 6-(2-chlorobenzyl)-5,6,7,7a-tetrahydro-4H-thieno[2,3-c ]pyridine-2-one in 50 ml of tetrahydrofuran. After 15 minutes, stirring, still at 0° C., 2.1 ml (0.020 mole) of isobutyryl chloride are introduced dropwise and the medium is then left stirring for 1 hour at room temperature. 2 volumes of water are then introduced and the final product is extracted in ethyl acetate; the oil, isolated after washing the organic phase with water and evaporating off the solvent, is chromatographed on a silica column, eluting with a toluene/ethyl acetate mixture (9:1 v/v). The hydrochloride of the final product melts at 111° C. Yield 40%.

$^1$H NMR (250MHz, DMSO-d$_6$): 1.20(d,6H); 2.80–2.90 (m, 1H); 2.90–3.15(m,1H); 3.45–3.70(m,3H); 4.35(s,2H); 4.59(s,2H); 6.62(s,1H); 7.40–7.65(m,3H); 8.05–8.15(m,1H).

EXAMPLE 24

Compound of formula I in which Z=S; m=2, n=1; R$_2$=H; R'=2-ClC$_6$H$_4$; R$_1$=C(CH$_3$)$_3$ (reference SR 26808).

7.74 ml (0.0124 mole) of a 1.6M solution of butyllithium in hexane are added dropwise at 0° C. to a solution of 3.3 g (0.0118 mole) of 6-(2-chlorobenzyl)-5,6,7,7a-tetrahydro-4H-thieno[2, 3-c]pyridine-2-one in 35 ml of tetrahydrofuran.

After 15 minutes, stirring, still at 0° C., 1.48 ml (0.0120 mole) of pivaloyl chloride are introduced dropwise and the medium is then stirred overnight at room temperature. 2 volumes of water are then introduced and the final product is extracted in ethyl acetate; the oil, isolated after washing the organic phase with water and evaporating off the solvent, is chromatographed on a silica column, eluting with a toluene/ethyl acetate mixture (9:1 v/v). The hydrochloride of the final product, prepared in ethyl ether, isolated in a 29% yield, melts at 145° C.

$^1$H NMR (250MHz, DMSO-d$_6$): 1.27(s,9H); 2.87–2.99(m,2H); 3.39–3.57(m,2H); 4.33(s,2H); 4.58(s,2H); 6.63(s,1H); 7.43–7.60(m,3H); 8.05–8.08(m,1H).

EXAMPLE 25

N-Oxide of the compound of formula I in which Z=S; m=1; n=2; R$_2$=H; R'=2-ClC$_6$H$_4$; R$_1$=CH$_3$ (hydrochloride: reference SR 26621).

10 g (0.031 mole) of 5-(2-chlorobenzyl)-4,5,6,7-tetrahydrothieno[3,2-c]pyrid-2-yl acetate, obtained according to Example 1, are dissolved in 30 ml of chloroform, and 6.3 g (0.031 mole) of 85% pure meta-chloroperbenzoic acid are introduced portionwise into the solution, maintained at 0° C. After the addition is complete, the mixture is stirred at room temperature for 2 hours before the introduction of at least 0.04 mole of HCl in the form of a 2N solution in ethyl ether. The precipitate formed, consisting of the hydrochloride of the N-oxide, is isolated by filtration.

M.p. 112° C.—yield 79%.

$^1$H NMR (80MHz, DMSO-d$_6$): 2.45(s,3H); 3.10–3.45(m,2H); 4.02–4.50(m,2H); 4.72–5.11(m,2H); 5.33(s,2H); 6.72(s,1H); 7.42–7.90(m,3H); 7.95–8.21(m,1H).

EXAMPLES 26 to 39

The N-oxides of the following compounds of formula I were prepared by applying the procedure of Example 25 to the heterocyclic amines of formula I obtained according to the methods described in the above examples.

| Ex. | SR | Z | m | n | R$_2$ | R' | R$_1$ | F (hydrochloride) | Yield of salt |
|---|---|---|---|---|---|---|---|---|---|
| 26 | 26832 | S | 1 | 2 | H | 2-ClC$_6$H$_4$ | C$_3$H$_7$ | 128° C. | 86% |
| 27 | 26833 | S | 1 | 2 | H | 2-ClC$_6$H$_4$ | CH(CH$_3$)$_2$ | 140° C. | 67% |
| 28 | 26831 | S | 1 | 2 | H | 2-ClC$_6$H$_4$ | C(CH$_3$)$_3$ | 158° C. | 87% |
| 29 | 26725 | S | 1 | 2 | COOCH$_3$ | 2-ClC$_6$H$_4$ | CH$_3$ | 100° C. | 62% |
| 30 | 26914 | S | 1 | 2 | 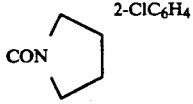 | 2-ClC$_6$H$_4$ | CH$_3$ | 144° C. | 63% |
| 31 | 26986 | S | 1 | 2 | H | C$_6$H$_5$ | C(CH$_3$)$_3$ | 175° C. | 82% |
| 32 | 27354 | S | 1 | 2 | CH$_3$ | C$_6$H$_5$ | C(CH$_3$)$_3$ | 105° C. | 71% |
| 33 | 26977 | S | 1 | 2 | H | 4-ClC$_6$H$_4$ | C(CH$_3$)$_3$ | 160° C. | 83% |
| 34 | 27262 | S | 1 | 2 | H | 4-OCH$_3$C$_6$H$_4$ | C(CH$_3$)$_3$ | 165° C. | 81% |
| 35 | 27165 | S | 1 | 2 | H | CH$_3$ | C(CH$_3$)$_3$ | 186° C. | 98% |
| 36 | 27325 | S | 1 | 2 | H | C$_3$H$_7$ | C(CH$_3$)$_3$ | 116° C. | 79% |
| 37 | 26916 | S | 1 | 2 | H | 2-ClC$_6$H$_4$ | C$_6$H$_5$ | 170° C. | 88% |
| 38 | 26998 | S | 2 | 1 | H | 2-ClC$_6$H$_4$ | C(CH$_3$)$_3$ | 118° C. | 48% |
| 39 | 26993 | O | 1 | 2 | H | 2-ClC$_6$H$_4$ | C(CH$_3$)$_3$ | 160° C. | 90% |

$^1$H NMR spectra of the hydrochlorides of these products:

| Ex. | δ (ppm): |
|---|---|
| 26 | (250 MHz, CDCl$_3$): 1.00(t, 3H); 1.74(q, 3H); 2.52 (t, 2H); 3.02–3.12(m, 2H); 3.38–3.51(m, 1H); 3.93–4.04(m, 1H); 4.48–4.59(m, 2H); 4.79(d, 1H); 5.31(d, 1H); 5.42(d, 1H); 6.34(s, 1H); 7.39–7.50 (m, 3H); 8.18–8.21(m, 1H). |
| 27 | (250 MHz, CDCl$_3$): 1.29(d, 6H); 2.79(h, 1H); 3.05–3.14(m, 1H); 3.43–3.49(m, 1H); 3.91–4.02(m, 1H); 4.51–4.57(m, 2H); 4.81(d, 1H); 5.32(d, 1H); 5.43 (d, 1H); 6.36(s, 1H); 7.42–7.51(m, 3H); 8.21–8.24 (m, 1H). |
| 28 | (250 MHz, CDCl$_3$): 1.30(s, 9H); 3.03–3.10(m, 1H); 3.39–3.51(m, 1H); 3.99–4.01(m, 1H); 4.48–4.61 (m, 2H); 4.81(d, 1H); 5.32(d, 1H); 5.42(d, 1H); 6.35(s, 1H); 7.39–7.50(m, 3H); 8.17–8.21(m, 1H). |
| 29 | (80 MHz, CDCl$_3$): 2.35(s, 3H); 2.79–3.31(m, 2H); 3.95(s, 3H); 4.20–5.55(m, 4H); 6.55(s, 1H); 6.98(s, 1H); 7.54–7.87(m, 3H); 8.29–8.56(m, 1H). |
| 30 | (80 MHz, DMSO-d$_6$): 1.55–1.93(m, 4H); 2.26(s, 3H); 3.48–5.32(m, 10H); 6.33 and 6.39(2s, 1H); 6.55 and 6.60(2s, 1H); 7.25–7.96(m, 4H). |
| 31 | (80 MHz, DMSO-d$_6$): 1.37(s, 9H); 3.14–3.36(m, 2H); 4.07–4.26(m, 2H); 4.51(d, 1H); 4.98(d, 1H); 5.18 (s, 2H); 6.74(s, 1H); 7.59–7.87(m, 5H). |
| 32 | (250 MHz, DMSO-d$_6$): 1.25(s, 9H); 1.80–1.90(m, 3H); 3.00–3.15(m, 1H); 3.15–3.35(m, 2H); 4.20–4.40 (m, 1H); 4.55–4.80(m, 1H); 4.85–4.95(d, 1H); 5.15–5.4(m, 1H); 6.55(d, 1H); 7.40–7.70(m, 4H); 7.85(s, 1H). |
| 33 | (250 MHz, CDCl$_3$): 1.32(s, 9H); 3.00(m, 1H); 3.31 (m, 1H); 4.06–4.39(m, 4H); 4.51(d, 1H); 4.86 (d, 1H); 5.18(d, 1H); 5.29(d, 1H); 6.30(s, 1H); 7.35(d, 2H); 7.67(d, 2H). |
| 34 | (250 MHz, DMSO): 1.24(s, 9H); 3.10(m, 2H); 3.78 (s, 3H); 4.03(m, 2H); 4.41(d, 1H); 4.87(s, 1H); 5.08(s, 2H); 6.64(s, 1H); 7.07(d, 2H); 7.62 (d, 2H). |
| 35 | (250 MHz, DMSO): 1.27(s, 9H); 3.11(m, 1H); 3.33 (m, 1H); 3.66(s, 1H); 3.99(m, 1H); 4.12(m, 1H); 4.82(s, 2H); 6.63(s, 1H). |
| 36 | (250 MHz, DMSO-d$_6$): 0.95(t, 3H); 1.25(s, 9H); 1.80–2.95(m, 2H); 3.00–3.30(m, 2H); 3.75–3.85 (m, 2H); 3.85–3.97(m, 1H); 4.10–4.20(m, 1H); 4.75(s, 2H); 6.60(s, 1H). |
| 37 | (250 MHz, DMSO-d$_6$): 3.12–3.32(m, 2H); 4.05–4.40 (m, 2H); 4.77(d, 1H); 5.05(d, 1H); 5.30(s, 2H); 6.87(s, 1H); 7.50–8.35(m, 9H). |
| 38 | (80 MHz, DMSO-d$_6$): 1.35(s, 9H); 3.30–3.50(m, 2H); 4.10–4.35(m, 2H); 5.00(s, 1H); 5.10(s, 1H); 5.35 (s, 2H); 6.80(s, 1H); 7.60–7.75(m, 3H); 8.00–8.00(m, 1H). |
| 39 | (80 MHz, DMSO-d$_6$): 1.35(s, 9H); 3.05–3.30(m, 2H); 4.20–4.40(m, 2H); 4.80(s, 1H); 5.00(s, 1H); 5.35 (s, 2H); 6.10(s, 1H); 7.60–7.80(m, 3H); 8.10–8.25(m, 1H). |

EXAMPLE 40

Compound of formula I in which Z=S; m=1, n=2; R$_2$=H; R'=2-ClC$_6$H$_4$; R$_1$=C$_2$H$_5$O (reference Sr 26893).

4.15 ml of a 1.6M solution of butyllithium in hexane are introduced dropwise at 0° C. into a solution of 1.78 g (0.063 mole) of 5-(2-chlorobenzyl)-5,6,7,7a-tetrahydro-4H-thieno[3,2-c]pyridine-2-one in 30 ml of tetrahydrofuran. After 15 minutes' stirring, still at 0° C., 0.67 ml (0.00695 mole) of ethyl chloroformate is added and the medium is then left stirring for several hours at room temperature. After the addition of 2 volumes of water, the final product is extracted with dichloromethane and purified, after evaporating off the solvent, by chromatography on a silica column, eluting with a toluene-/ethyl acetate mixture (9:1 v/v). 1.4 g of the desired product are thereby obtained in the form of a yellow oil. The oxalate, the salt formed from 1 molecule of oxalic acid and 1 molecule of amine of formula I, prepared in ethanol, melts at 202° C.

Amine of formula I: $^1$H NMR (80MHz, CDCl$_3$): 1.37 (t,3H); 2.79–2.85(m,4H); 3.52(s,2H); 3.80(s,2H); 4.31 (q,2H); 6.33(s,1H); 7.18–7.38(m,3H); 7.51–7.55(m,1H).

EXAMPLE 41

Compound of formula I in which Z=S; m=1; n=2; R$_2$=H; R'=2-ClC$_6$H$_4$; R$_1$=(CH$_3$)$_2$CH—CH$_2$—O (reference SR 26896).

Prepared in a 49% yield by the method of Example 40, this compound gives an oxalate which melts at 168° C. Amine of formula I: $^1$H NMR (250MHz, DMSO-d$_6$): 0.92(d,6H); 1.96(m,1H); 2.79–2.82(m,2H); 2.97–3.01(m,2H); 3.62(s,2H); 3.95(s,2H); 4.03(d,2H); 6.55(s,1H); 7.34–7.49(m,3H); 7 56–7.60(m,1H).

EXAMPLE 42

Compound of formula I in which Z=S; m=1; n=2; R$_2$=H; R'=2-ClC$_6$H$_4$; R$_1$=(CH$_3$)$_3$CO (reference SR 26887).

33.2 ml of 1N aqueous NaOH solution are introduced into a solution of 5 g (0.0158 mole) of 5-(2-chlorobenzyl)-5,6,7,7a-tetrahydro-4H-thieno [3,2-c]pyridine-2-one in 50 ml of dioxane, followed by 5.17 g (0.0237 mole) of di-tert-butyl carbonate. After stirring for a few hours at room temperature, 2 volumes of water and 2 volumes of ethyl acetate are added; the organic phase is separated after settling has taken place, washed and dried, and the oil isolated after removal of the solvent is purified by chromatography on a silica column, eluting with a toluene/ethyl acetate mixture (9:1 v/v).

4.6 g of the desired product are thereby obtained in the form of a yellow oil; the oxalate which crystallizes in acetone, melts at 166° C.

Amine of formula I: $^1$H NMR (80MHz, CDCl$_3$): 1.56(s,9H); 2.83(m,4H); 3.53(s,2H); 3.81(s,2H); 6.32(s,1H); 7.22–7.34(m,4H).

EXAMPLE 43

Compound of formula I in which Z=S; m=1; n=2; R$_2$=H; R′=2-ClC$_6$H$_4$; R$_1$=C$_6$H$_5$CH$_2$O (reference SR 26888).

50 ml of a solution in tetrahydrofuran of 5 g (0.0179 mole) of 5-(2-chlorobenzyl)-5,6,7,7a-tetrahydro4H-thieno[3,2-c]pyridine-2-one are introduced dropwise at 5° C. into 20 ml of a solution of 2.11 g (0.0188 mole) of potassium tert-butylate in tetrahydrofuran. After 15 minutes' stirring, 3.2 g (0.0188 mole) of benzyl chloroformate are introduced into the medium, still at this temperature. After 2 hours' stirring at room temperature, 2 volumes of water and 2 volumes of ethyl acetate are added. After stirring, the organic phase is separated, washed with water and dried over anhydrous Na$_2$SO$_4$ and the solvent is removed. The residual oil is purified by chromatography on a silica column with ethyl acetate as eluent, to give a 98% yield of the final product in the form of an oil. The oxalate of the desired product melts at 171° C.

Amine of formula I: $^1$H NMR (250MHz, DMSO-d$_6$): 2.79(m,2H); 2.95(m,2H); 3.60(s,2H); 3.93(s,2H); 5.29(s,2H); 6.56 (s,1H); 7.33–7.49(m,8H); 7.55–7.59(m,1H).

EXAMPLE 44

Compound of formula I in which Z=S; m=2; n=1; R$_2$=H; R′=2-ClC$_6$H$_4$; R$_1$=(CH$_3$)$_2$CH—CH$_2$—O (reference SR 26809).

This compound was prepared by the method described in Example 40. The oxalate of the desired product, crystallized in acetone, melts at 168° C. Yield 48%.
$^1$H NMR (250MHz, DMSO-d$_6$): 0.92(d,6H); 1.96(m,1H); 2.79–2.82(m,2H) 2.97–3.01(m,2H); 3.62(s,2H); 3.95(s,2H); 4.03 (d,2H); 6.55(s,1H); 7.34–7.49(m,3H); 7.56–7.60 (m,1H).

EXAMPLES 45 to 48

The N-oxides of the compounds of Examples 40 to 44 were prepared by the method described in Example 24 to the corresponding amines. The characteristics of the products obtained appear in the following table.

| Ex. | SR | Z | m | n | R$_2$ | R′ | R$_1$ | F (hydrochloride) | Yield of salt |
|---|---|---|---|---|---|---|---|---|---|
| 45 | 26894 | S | 1 | 2 | H | 2-ClC$_6$H$_4$ | C$_2$H$_5$—O | 130° C. | 94% |
| 46 | 26898 | S | 1 | 2 | H | 2-ClC$_6$H$_4$ | (CH$_3$)$_2$CHCH$_2$—O | 140° C. | 56% |
| 47 | 26891 | S | 1 | 2 | H | 2-ClC$_6$H$_4$ | C$_6$H$_5$—CH$_2$—O | 113° C. | 66% |
| 48 | 26889 | S | 1 | 2 | H | 2-ClC$_6$H$_4$ | (CH$_3$)$_3$C—O | 126° C. | 20% |

The characteristics of the $^1$H NMR spectra of the hydrochlorides of these N-oxides are as follows:

| Ex. | δ (ppm): |
|---|---|
| 45 | (250 MHz, CDCl$_3$): 1.38(t, 3H); 3.00–3.20(m, 1H); 3.42–3.62(m, 1H); 3.98–4.12(m, 1H); 4.35(q, 2H); 4.51–4.57(m, 2H); 4.74(d, 1H); 5.31(d, 1H); 5.46 (d, 1H); 6.36(s, 1H); 7.41–7.50(m, 3H); 8.19–8.23(m, 1H). |
| 46 | (250 MHz, CDCl$_3$): 0.97(d, 6H); 1.99–2.05(m, 1H); 2.93–3.13(m, 1H); 3.34–3.51(m, 1H); 4.02–4.05 (m, 3H); 4.51–4.61(m, 2H); 4.74(d, 1H); 5.31 (d, 1H); 5.43(d, 1H); 6.35(s, 1H); 7.39–7.48 (m, 3H); 8.15–8.19(m, 1H). |
| 47 | (250 MHz, DMSO-d$_6$): 3.07–3.25(m, 2H); 4.03–4.31 (m, 2H); 4.66–4.92(m, 2H); 5.20(s, 2H); 5.30 (s, 2H); 6.71(s, 1H); 7.39–7.66(m, 8H); 7.94–7.97(m, 1H). |
| 48 | (250 MHz, DMSO-d$_6$): 1.49(s, 9H); 2.93–3.67(m, 2H); 3.95–4.42(m, 2H); 4.57–5.02(m, 2H); 5.24(s, 2H); 6.66(s, 1H); 7.54–7.62(m, 3H); 8.05–8.25(m, 1H). |

EXAMPLE 49

Methyl sulphate of the 5-methylammonium derivative of the compound of formula I in which Z=S; m=1; n=2; R$_2$=H; R′=2-ClC$_6$H$_4$; R$_1$=(CH$_3$)$_3$C (reference SR 27168). 8.35 g (0.0229 mole) of 5-(2-chlorobenzyl)-4,5,6,7-tetrahydrothieno[3,2-c]pyridyl-2 t-butyrate are dissolved in 85 ml of acetone with 2.89 g (0.0229 mole) of dimethyl sulphate; after 12 hours' stirring at room temperature, the volatile products are removed under reduced pressure and the residue is chromatographed on a silica column, eluting with a dichloromethane/methanol mixture (9:1 v/v). The methyl sulphate melts at 60° C.; yield 43%.

Results of the pharmacological experiments demonstrating the activities of the compounds according to the invention are given below.

a) In vitro inhibition of elastase enzymatic activity.

The variation of the rate of hydrolysis of a substrate specific of elastases was studied in the presence and absence of the test compound according to a conventional technique. The experiments were performed with porcine pancreatic elastase, and human neutrophil elastase extracted from purulent sputum; the enzyme substrate was a chromogenic tetrapeptide, N-succinyl-L-alanyl-L-alanyl-L-propyl-L-leucyl-p-nitroanilide, designated Suc-Ala-Ala-Pro-LeupNA, which, on hydrolysis, liberates p-nitroaniline, the appearance of which in the medium is followed in a spectrophotometer; alpha$_1$-antitrypsin was used as a standard inhibitor. The experiments were performed at 25° C., the spectrophotometric measurement being made at 410 nm.

The solution of substrate was prepared by dissolving 5.8 mg of anilide in 20 ml of buffer solution containing 24.22 g/l of Tris-HCl with 754 mg/l of CaCl$_2$, adjusted to pH 8.8.

The solution of enzyme in the same buffer was at a concentration of 0.1 g/l, while the solutions of test compound in the same buffer were at concentrations of between 0.1 mM and 0.01 µM.

200 µl of solution of substrate, 75 µl of buffer solution and 200 µl of solution of the test compound, or of buffer solution in the case of the controls, were mixed in tubes. After 20 minutes at 25° C., the tube was placed in the recording spectrophotometer and 25 µl of the solution of enzyme were added to this medium; the change in the optical density ΔOD was recorded for 30 seconds.

The percentage inhibition is defined as the difference between the change in OD for the control sample and that for the test sample, divided by the change for the control and multiplied by 100.

$$\% I = \frac{\Delta OD(\text{control}) - \Delta OD(\text{test})}{\Delta OD(\text{control})} \times 100$$

In Tables I and II, the concentrations, in the final solution, of the test compound, giving a percentage inhibition of 50% (IC$_{50}$) are presented.

TABLE I

Enzyme: porcine pancreatic elastase

| Test compound (SR) or PCR | IC$_{50}$ (µM) | Test compound (SR) | IC$_{50}$ (µM) | Test compound (SR) | IC$_{50}$ (µM) |
|---|---|---|---|---|---|
| α$_1$-Antitrypsin | 1.2 | 26842 | 10 | 26986 | 2.2 |
| PCR 4094 | 2 | 26861 | 6.4 | 27354 | 10 |
| 26772 | 5.8 | 26938 | 3.6 | 26977 | 2.5 |
| 26769 | 7 | 26886 | 2.9 | 27262 | 1 |
| 26767 | 4.8 | 26913 | 32 | 27165 | 10 |
| 26829 | 8 | 26862 | 4 | 27325 | 15 |
| 26827 | 9 | 26832 | 7 | 26998 | 2.2 |
| 27261 | 4.5 | 26833 | 6 | 26993 | 1.7 |
| 27319 | 4.5 | 26831 | 5 | 26894 | 24 |
| 26984 | 3.6 | 26914 | 25 | 27168 | 1.6 |
| 27318 | 10 | | | | |

TABLE II

Enzyme: human leucocyte elastase

| Test compound (SR) or PCR | IC$_{50}$ (µM) | Test compound (SR) | IC$_{50}$ (µM) | Test compound (SR) | IC$_{50}$ (µM) |
|---|---|---|---|---|---|
| α$_1$-Antitrypsin | 1.2 | 27318 | 3 | 27354 | 2.6 |
| PCR 4094 | 3.5 | 26842 | 3.2 | 26977 | 1.8 |
| 26772 | 2.6 | 26861 | 2.6 | 27262 | 2.6 |
| 26769 | 30 | 26938 | 3.1 | 27165 | 1.2 |
| 26767 | 3.4 | 26886 | 30 | 27325 | 0.7 |
| 26829 | 24 | 26862 | 50 | 26998 | 2.2 |
| 26827 | 3.4 | 26832 | 5.6 | 26993 | 3.1 |
| 27261 | 3.2 | 26833 | 3.6 | 26887 | 50 |
| 27319 | 3.4 | 26831 | 2.5 | 27889 | 50 |
| 26984 | 2.6 | 26986 | 2.3 | | | b) Platelet aggregation-inhibitory activity in rats.

According to a technique described, in particular, in FR-A-2,567,901, the inhibition of platelet aggregation in blood taken from treated animals, when ADP or collagen is added thereto was studied; the test compounds were administered orally. SR 26766 and SR 26827 have especially exceptional activity since, at a dose of 100 mg/kg, they give a percentage inhibition of aggregation, respectively, of 61% and 48% for ADP and 62% and 21% for collagen.

We claim:

1. A compound of formula wherein R$_1$ is selected from the groups R$_3$ and OR$_3$, in which R$_3$ is selected from C$_1$ to C$_6$ alkyl, phenyl and benzyl R is selected from H and the groups CHR$_2$R', in which R$_2$ is selected from H, C$_1$ to C$_4$ alkyl, the group —COOR$_4$, R$_4$ being H, C$_1$ to C$_4$ alkyl and benzyl and the group —CONR$_5$R$_6$, R$_5$ and R$_6$, independently of one another, being H, C$_1$ to C$_4$ alkyl and benzyl, or R$_5$ and R$_6$, with the nitrogen to which they are attached, forming a saturated C$_4$-C$_8$ heterocycle; R' is H, C$_1$ to C$_4$ alkyl and phenyl optionally substituted with one or more substituents selected from halogen atoms, C$_1$ to C$_4$ alkyl, C$_1$ to C$_4$ alkoxy, trifluoromethyl and nitro; Z is S or O; m and n, which may be identical or different, are 1 or 2, or its salts with pharmaceutically acceptable acids, the N-oxides of compound of formula I and its salts with pharmaceutically acceptable acids and the quaternary ammonium derivatives resulting from condensation of a compound of formula I with a C$_1$ to C$_4$ alkyl halide or sulphate, 2. A compound according to claim 1, wherein R$_1$ is C$_1$ to C$_6$ alkyl.

3. A compound according to claim 1, wherein : R' is phenyl optionally substituted with one or more substituents selected from halogen atoms, C$_1$ to C$_4$ alkyl, C$_1$ to C$_4$ alkoxy, trifluoromethyl and nitro and R$_2$ is selected from COOR$_4$ and CONR$_5$R$_6$.

4. A compound according to claim 1 wherein : R' is phenyl optionally substituted with one or more substituents selected from halogen atoms a C$_1$ to C$_4$ alkyl, C$_1$ to C$_4$ alkoxy, trifluoromethyl and nitro, and R$_2$ is H or a C$_1$ to C$_4$ alkyl.

5. A compound according to claim 1, wherein m is 1 and n is 2.

6. A compound according to claim 1, wherein m is 2 and n is 1.

7. A compound according to claim 1, wherein R$_1$ is C$_1$ to C$_6$ alkyl, m is 1 and n is 2, R' is phenyl optionally substituted and R$_2$ is COOR$_9$.

8. A compound according to claim 1 of formula I, wherein Z is S, R$_1$ is C$_1$ to C$_6$ alkyl, m is 1 or 2, R$_2$ is H and R' is phenyl optionally substituted, or its pharmaceutically acceptable salts.

9. A pharmaceutical composition comprising a compound according to claim 1 and a pharmaceutically acceptable carrier or diluent.

10. A pharmaceutical composition comprising a compound according to claim 8 and a pharmaceutically acceptable carrier or diluent.

* * * * *